United States Patent [19]

McNamee

[11] 4,254,772
[45] Mar. 10, 1981

[54] HAIRPIECE RETENTION SYSTEM AND METHOD OF APPLYING SAME

[76] Inventor: Thomas C. McNamee, 2451 Monaco Dr., Channel Island, Calif. 93030

[21] Appl. No.: 91,265

[22] Filed: Nov. 5, 1979

[51] Int. Cl.³ .............................................. A61B 17/00
[52] U.S. Cl. .................................................. 128/330
[58] Field of Search ................. 128/330, 329 R, 335.5, 128/1 R; 3/1; 132/53; 46/172

[56] References Cited

U.S. PATENT DOCUMENTS

| | | | |
|---|---|---|---|
| 3,858,245 | 1/1975 | Nate et al. | 128/329 X |
| 4,054,954 | 10/1977 | Nakayama et al. | 128/330 X |
| 4,092,739 | 6/1978 | Clemens et al. | 128/330 X |

Primary Examiner—Robert W. Michell
Assistant Examiner—Michael H. Thaler
Attorney, Agent, or Firm—Booker T. Hogan, Jr.

[57] ABSTRACT

A surgically implanted suture retained by one or more epi-surface retention strands and bound by ties is disclosed which serves to provide a permanent hairpiece retention system.

5 Claims, 7 Drawing Figures

HAIRPIECE RETENTION SYSTEM AND METHOD OF APPLYING SAME

FIELD OF THE INVENTION

This invention relates generally to the provision of a cosmetic remedy for the anguish experienced by those concerned with the balding process. More particularly, the invention discloses a surgical system for firmly attaching an artificial hairpiece to the scalp of a person.

BACKGROUND ART

For centuries, those afflicted with hair loss or baldness have made anguished, but futile searches for a remedy. All sorts of chemical treatments have been tried, without success, to cause hair to grow where it has failed to grow. In recognition of the futility of this approach, efforts have been expanded to provide suitable methods for covering bald spots or areas of the scalp by transplanting hair in bald areas of the scalp or by attaching hair or artificial pieces to the scalp.

An example of the former method is the punch autograph technique wherein grafts containing hair follicles are removed from a donor site and placed in the hairless recipient area. While this technique has shown promise as it has been refined, complications, such as syncope, bleeding, edema, infection, and scarring still occur with an unacceptable frequency.

A method which combines the concept of implantation with the use of artificial hair is disclosed in U.S. Pat. No. 3,003,155 issued to F. C. Mielzynski et al in October, 1961. This method was also plagued with dart rejection and infection problems.

The closest prior art known to me is contained in U.S. Pat. No. 3,553,737 issued to Jack Bauman in January of 1971. This patent discloses and claims a method of applying hair to the scalp of a human being which utilizes the latter approach mentioned above.

The "737" patent discloses the use of a continuous teflon-coated wire suture embedded into the scalp in an "in-and-out" technique which forms anchor points at the surface of the scalp where the suture breaks the surface at acute angles. A woven grid used to retain hair tufts or flags is subsequently attached to the anchor points.

Hairpieces attached to the scalp in accordance with the teachings of the "737" patent are known to be quite permanent. However, stresses imparted to the scalp by tension and/or wind frictional forces tend to induce painful sensations in the scalp and ultimately lead to complications such as bleeding and infection.

These problems are attributed to the fact that the Bauman method utilizes a multiplicity of skin punctures at acute angles to the surface of the skin for the purpose of embedding the wire in the skin. Bauman apparently failed to recognize the potential for and protect against continuous tears of the skin when stress is applied to the suture running through the punctures which form slits in the skin along cleavage lines of the scalp. Punctures at the acute angles to the cleavage lines tend to exacerbate the problem attendant to the insertion of a foreign material in the scalp and preclude complete healing of the skin about the suture material.

SUMMARY OF THE INVENTION

It is a general purpose of this invention to provide a system for permanently affixing a hairpiece to a human scalp which avoids most, if not all of the disadvantages of the prior art while retaining the advantages of the prior art.

In achieving this purpose and other objectives which shall be apparent, I have invented an improved hairpiece retention system and surgical method for applying the system to the scalp of a human being.

The hair retention system of my invention is comprised of three elements: The first element is a continuous suture of nonabsorbable, nonreactive, monofilament material surgically implanted in the layers of the integument, which covers the cranial periosteum, to circumscribe the hairless area of the scalp. This material, called the "implanted suture," penetrates or punctures the epidermis orthogonally and defines a parabolical path as it passes through the dermis, subcutaneous fascia, and galea aponeurotica to return to the surface of the epidermis where loops are formed by subsequent penetrations of the integument. Each puncture of the epidermis serves as an entrance and exit point for the implanted suture, thereby minimizing the total number of external ruptures of the integument required to provide contact points or loops at the outer surface of the epidermis; the second element of my system referred to as the "retention strand" is a continuous mono-filament suture material threaded through the loops of the implanted suture at the surface of the epidermis which retains the loops of the implanted suture above the epidermis; and the third element of my system is a series of ties which bind the loops of the implanted surface beneath the retention strand and extend in an outward direction from the surface of the epidermis to provide a means for attaching a hairpiece to the hairpiece retention system. It is applied to the scalp of a recipient using standard surgical methods while the recipient is under the effects of a local anaesthetic.

Stresses created by tension and/or shear forces applied to hairpieces attached to my system are evenly distributed over the entire scalp, therefore, the stress per unit area is minimized.

The penetration angles of the implanted sutures serve to minimize cleavage of the integument and thereby reduce lacerations and infection attendant unto the insertion of a foreign material into the skin.

It is, therefore, an object of this invention to provide a means for permanently attaching a hairpiece to the head of a person.

A further objective of this invention is to provide a system for attaching a hairpiece to the head of a person which does not irritate the integument which covers the skull.

A still further objective of this invention is to minimize stresses imparted to the skin when a hairpiece is attached thereto by surgical means.

That I have accomplished these objectives while avoiding the disadvantages of the prior art and retaining its advantages will be apparent from the following drawings and detailed description of my invention.

DETAILED DESCRIPTION OF THE INVENTION

In order to achieve the above-stated objectives and avoid the disadvantages of prior art systems which I attribute to high specific stresses, I have devised a hairpiece retention system and a method for surgically implanting the system in the layers of the integument (scalp) which cover the cranial bone of a person, which evenly distributes stresses over a large area thereby minimizing specific stress which tend to promote lacerations of the integument. My system has been totally accepted by all persons who have tested it without exhibiting any evidence of complications. It is adopted for attaching an artifical hairpiece to the epicranial portion of the scalp which does not have to be removed, although it may be removed.

Figure 1:
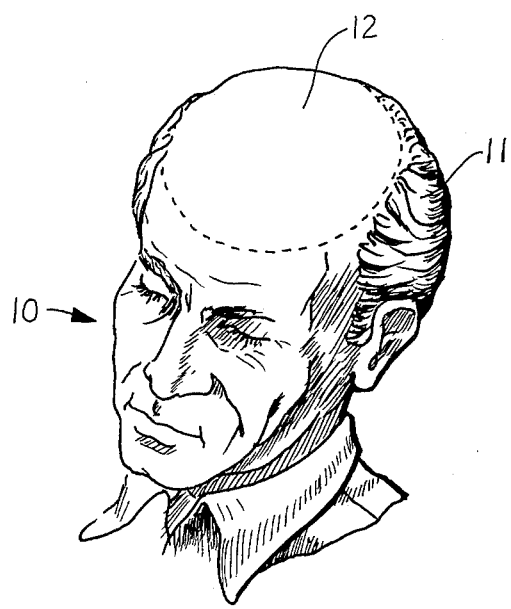
FIG. 1 is a perspective view of the head of a person who has lost his hair from the area circumscribed by dashes.

Referring to FIG. 1, a typical profile of a person 10, whose hair 11 has ceased growing in the epicranial portion of the scalp 12, especially suitable for receiving my invention is shown. My system provides a means for attaching a hairpiece to the scalp which mates with and looks like the residual hair 11.

Figure 2:
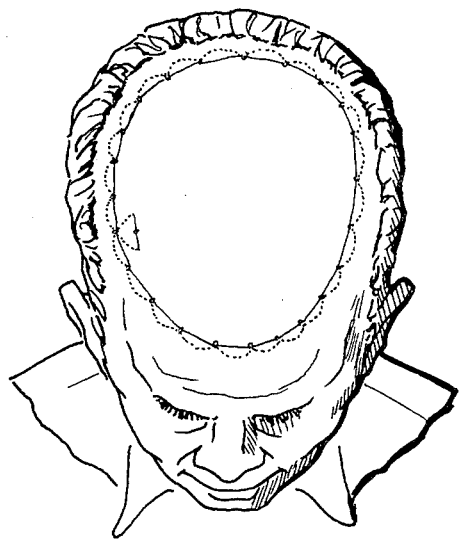
FIG. 2 is a perspective view of the head of a person having a hairpiece retention system comprised of one continuous retention strand and one continuous implanted suture.
Figure 3:
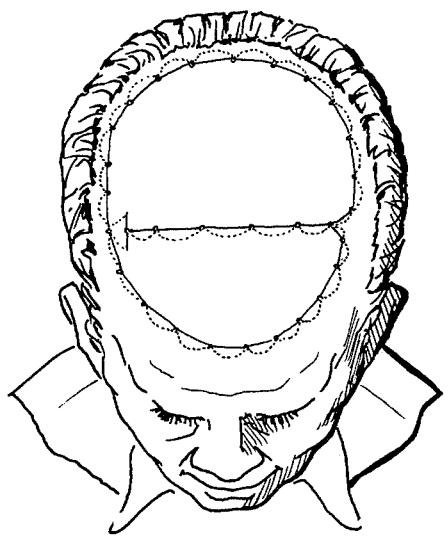
FIG. 3 is a perspective view of the head of a person having a hairpiece retention system comprised of two retention strands and a single continuous implanted suture.
Figure 4:
FIG. 4 is a perspective view of the head of a person having a hairpiece retention system comprised of four retention strands.
Figure 5:
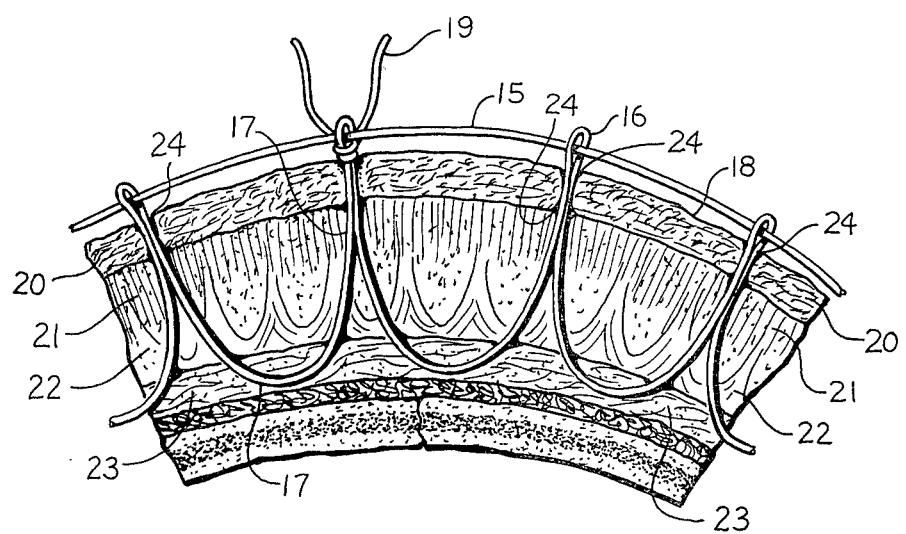
FIGS. 5 and 7 are expanded fragmentary cross-sections of a portion of the scalp of a person which shows the implanted suture, retention strand, and ties of the hair retention system.
Figure 7:
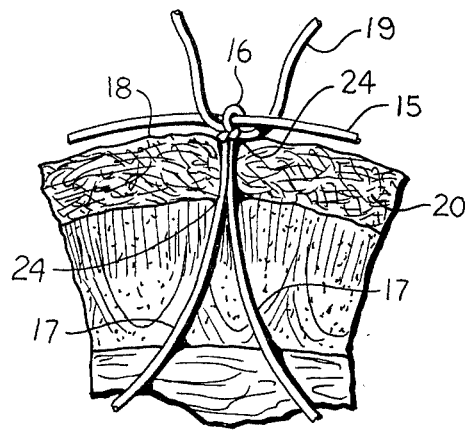
Figure 6:
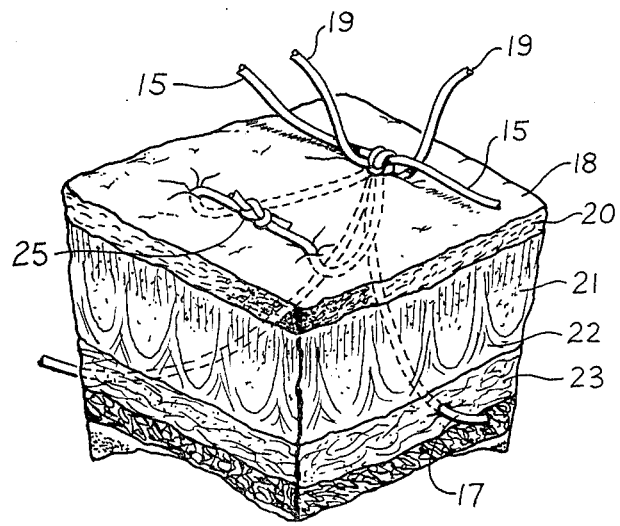
FIG. 6 is an expanded perspective view of a plug taken from the scalp of a person which shows the position of the terminal knot which secures the hair retention system.

Perspective views of three versions of my system, minus ties, are shown in FIGS. 2 through 4. Retention strands 15 running through loops 16, formed from a continuous implanted suture 17 of nonabsorbable, non-reactive, mono-filament materal surgically implanted into the integument are shown. The loops protrude from the epidermis at orthogonal angles with respect to the surface of the epidermis 18 and are bound by ties 19 which extend outward from the surface of the epidermis and provide a means for attaching a hairpiece (not shown) to the hairpiece retention system (see FIG. 5).

Each element of the system is made of nonabsorbable, nonreactive, monofilament suture material commonly utilized in surgical procedures. I prefer to use 00000 to 2.0 gage polypropylene marketed under the trade name "Prolene" by Ethicon Corporation. However, any sterile suture material is suitable.

Referring again to FIG. 5, the continuous implanted suture 17 is inserted into the epidermis 20 orthogonally to its surface 18 and defines or circumscribes a parabolical path through the dermis 21, subcutaneous fascia 22 and possibly through the galea aponeurotica 23 as it returns to the surface of the epidermis 18 where loops or contact points 16 are formed. It should be noted that the loops 16 are formed by causing the suture 17 to exit and reenter the epidermis 18 through the same punctures 24 of the epidermis. This feature minimizes the total number of ruptures of the epidermis and thereby reduces the propensity for infection to set in and promotes complete healing of the lacerations associated with punctures of the epidermis.

I have found that, by extending the implanted suture 17 through the firm, dense adipose layer of subcutaneous fascia 22 into the galea aponeurotica 23 (or epicranial aponeurosis), which consist of fibrous muscular tissue, in the above-described manner, I avoid excessive lacerations or tearing of the integument along cleavage lines which normally occur when one punctures the skin.

By employing a multiplicity of ties 19 which bind each of the contact points 16 about the retention strand 15, I avoid slippage which tends to preclude the integument from healing after the suture material has been implanted.

The number of contact points 16 having ties 19 which bind the hairpieces to the retention system serves to ensure an even distribution of any stresses which may be applied to the hairpieces retained by the system. As outward tension is applied in one area, the system distributes the resulting stress over the entire epicranial area by exerting inward tension over the nonstressed areas.

The implanted suture 17 is secured by a knot 25 placed within the perimeter of the retention strands 15 and is, therefore, hidden from view by the subsequently attached hairpiece.

While I have found a single retention strand or securing line to be adequate in most instances, it is sometimes desirable to utilize two retention strands, as shown in FIG. 3, or four retention strands, as shown in FIG. 4. In the first and last cases, the number of contact points will be essentially the same, while two retention strands will necessitate more contact points.

For added strength, I prefer to utilize a 0- to 1-gage suture material having a tensile strength of 10–20 lbf tests as the retention strand or runner.

In practice, I begin my implantation process by first shampooing and then shaving the scalp. I then mark the scalp to provide a guide for the insertion points for the implanted suture and apply a layer of an antiseptic solution to the scalp. After allowing the antiseptic solution to work for from one to three minutes, I then apply a local anaesthetic, such as a solution of 2 percent Xylocaine with epinephrine, and allow the anaesthetic to take effect (usually between 5 and 10 minutes). I then reapply an antiseptic and cover the head with a sterile drape to preclude contamination of the scalp as I fracture or puncture the skin.

Using a conventional one-half ($\frac{1}{2}$) to three-eighths ($\frac{3}{8}$) inch cutting trochar needle, I then insert the sutures to a level of approximately 1 centimeter in order to reach the galea aponeurotica without penetrating the periosteum. I prefer to start my sutures at the frontal temporal cranial junction of the skull and create a continuous series of contact points connected to each other by a parabolical implanted suture which ends at its point of origin.

While I have shown retention systems which circumscribe large areas of the scalp, my system may be utilized to cover smaller areas, such as scar tissue, where hair will not grow.

INDUSTRIAL APPLICABILITY

The provision of a hairpiece retention system in accordance with my invention will have commercial utility. My system and its method of application accomplishes that which others have sought to achieve without success. It is equally adaptable for use by male and female persons who want to provide hair coverings for bald or balding areas of the scalp.

Having completely disclosed my invention and provided teaching to enable others to make and utilize the same, the scope of my claims may now be understood, as follows.

I claim:

1. A hairpiece retention system suitable for being surgically implanted into the integument covering the head of a person, wherein said integument has an outer surface, an epidermis layer, a dermis layer, a subcutaneous fascia layer, and a galea aponeurotica layer of tissue, to provide a permanent means for attaching a hairpiece to said integument comprising:

a continuous implanted suture which enters and exits said integument to form a multiplicity of loops at said outer surface, one or more retention strands threaded through said loops which retain said loops at said outer surface, and a series of ties which bind said loops beneath said retention strands and extend outward from said loops to provide means for attaching a hairpiece to said retention system, characterized in that said suture penetrates and exits said epidermis layer, of said integument, through common punctures of said epidermis to form said loops at an orthogonal angle with respect to said epidermis layer and defines a parabolical path through the balance of said integument layers as it returns to said epidermis and exits said integument whereby additional loops are formed to circumscribe the area to be covered by said hairpiece.

2. The system of claim 1 wherein said implanted suture is a sterile nonabsorbable, nonreactive, monofilament polymeric material.

3. The system of claim 2 wherein said suture is polypropylene and said loops are retained at said outer surface with a single retention strand.

4. A method of firmly attaching a hairpiece to the scalp of a person having an outer surface layer and an integument comprising:

(a) surgically implanting a continuous suture in said integument characterized in that said suture forms loops at said outer surface, as it exits and reenters said integument, which orthogonally protrude from said surface;

(b) retaining said loops of said suture at said outer surface by threading one or more retention strands through said loops thereby providing a means for equally distributing stresses which may be subsequently applied to said loops; and (c) binding said loops beneath said retention strands with a series of ties which extend outward from said loops thereby providing means for attaching said hairpiece to said scalp.

5. The method of claim 4 wherein said loops are formed from said suture as it exits and reenters the epidermis of said integument through common punctures of said epidermis and said suture defines parabolical paths through the dermis, subcutaneous fascia and galea aponeurotica of said integument as it returns to the epidermis of said integument.

* * * * *